United States Patent [19]

Ishizaki et al.

[11] Patent Number: 5,413,929

[45] Date of Patent: May 9, 1995

[54] PROCESS FOR PRODUCING PLANTLETS WHEREBY THE FORMATION OF A CELL MASS IS INDUCED

[75] Inventors: Keiichirou Ishizaki; Noboru Onishi, both of Kitsuregawa, Japan

[73] Assignee: Kirin Beer Kabushiki Kaisha, Tokyo, Japan

[21] Appl. No.: 689,949

[22] Filed: May 28, 1991

[30] Foreign Application Priority Data

Sep. 30, 1989 [JP] Japan .................. 1-255440

[51] Int. Cl.$^6$ .................. C12N 5/00; C12N 5/02
[52] U.S. Cl. .................. 435/240.46; 435/240.4; 435/240.45; 435/240.54
[58] Field of Search ........... 435/240.4, 240.45, 240.46, 435/240.51, 240.54

[56] References Cited

FOREIGN PATENT DOCUMENTS

| | | | |
|---|---|---|---|
| 0172377A1 | 2/1986 | European Pat. Off. | A01G 7/00 |
| 0176162A1 | 4/1986 | European Pat. Off. | A01G 7/00 |
| 0275682A1 | 7/1988 | European Pat. Off. | A01G 7/00 |
| 0276575A1 | 8/1988 | European Pat. Off. | A01G 7/00 |
| 2539579 | 4/1984 | France | A01G 31/00 |
| 0056022 | 5/1986 | Japan | 435/240.45 |

OTHER PUBLICATIONS

Fujioka et al, Shoyakugaku Zasshi 41(4) 1987 pp. 308–312.
Evans et al, Handbook of Plant Cell Culture vol. 1, (1983), pp. 1–10.

*Primary Examiner*—Douglas W. Robinson
*Assistant Examiner*—Susan M. Dadio
*Attorney, Agent, or Firm*—Gray Cary Ware & Freidenrich

[57] ABSTRACT

The present invention relates to a process for producing plantlets using plant tissue culture techniques. The object of the invention is to provide a process which enables simple, highly reproducible and efficient production of seedlings in a large scale. The feature of the invention comprises culturing a root as an explant in a liquid medium containing at least inorganic salts, a carbon source and an auxin to induce the formation of a cell mass, and culturing the resultant cell mass in a redifferentiation medium containing at least inorganic salts and a carbon source, to produce plantlets.

7 Claims, No Drawings

PROCESS FOR PRODUCING PLANTLETS WHEREBY THE FORMATION OF A CELL MASS IS INDUCED

TECHNICAL FIELD OF THE INVENTION

The present invention relates to a process for producing a plantlet using plant tissue culture techniques.

BACKGROUND TECHNIQUES OF THE INVENTION

Recent developments in tissue culture techniques have been allowing commercial production of a variety of plants in a large scale. Particularly, in ornamental plants, the unit price of them is relatively high and therefore, propagation by means of tissue culture techniques is becoming a practical method, In plants of low price such as vegetables, on the other hand, commercial application of tissue culture techniques has not been accomplished yet due to low propagation efficiency, Propagation techniques using a tissue culture include propagation by cutting without callus formation; formation of adventitious shoots from a culture via callus formation or without callus formation, followed by rooting to produce plants; formation of somatic embryo from a callus to produce plants; formation of shoot primordium, and the like.

As an example of propagation by cutting, there has been known to propagate shoots of asparagus by culturing small lateral branches or nodes as an explant, followed by rooting to produce plants (Chee-kok Chin, HortScience 7(4): 590–591, 1982; Takayama S. et al., Japanese Patent Application Laid-Open-to-Public Publication No. 09722/1988). There has also been reported a method of propagation by cutting a plant derived from apical meristem culture of garlic on:a propagation medium (Bhojwani S., ScientiaiHorticulturae 13:47–52, 1980). Similar method has been reported about onion (Hussey G., Sci. Hortic., 9: 227–226, 1978). Furthermore, there have been many reports on other plants, for example, caladium (Hartman R. D., Phytopathology 64(2): 237–240, 1971), cordyline (Kunisaki J. T., HortScience 10 (6): 601–602, 1975), pineapple (Mathews V. H. et al., Scientia Hort. 11: 319–328. 1979), carnation (Fujino M. et al., Summary of Lectures at 1971 Spring Meeting of Japan Society of Horticulture, p 302–303), etc.

As examples of propagation via adventitious shoot formation, African violet, common gloxinia and the like may be mentioned (Start N. D. et al., HortScience 11 (3): 204–205, 1976; Haramaki C. , Int. Plant Prop. Soc. 21: 442–448, 1971). In these plants, plantlets are obtained by cutting the adventitious shoots, followed by rooting. Relating to the propagation via formation of a callus, there are many reports on plants such as strawberry (Osawa K. et al., The Bulletin of the Vegetable and Ornamental Crops Research Station, Ministry of Agriculture, Forestry and Fisheries, Series A, 1: 41–57, 1974) and tomato (Delanghe E. et al., Scientia Horticulturae, 4:221–227, 976).

As examples of somatic embryo formation, carrot (Kamata H., Chemical Regulation of Plants, Vol. 15 (2): 62–78, 1980), garlic (Abo El-Nil M., Plant Science Letters, 9: 259–264, 1977; Araki H. et al., Summary of Lectures at the 1988 Autumn Meeting of Japan Society of Horticulture, p.254–255), asparagus(Koumura H. et al., Summary of Lectures at the 1988 Spring Meeting of Japan Society of Horticulture, p.232–233; Hirata Y. et al., ibid., p. 230–231), and the like may be mentioned.

Above described methods of propagation are set forth for exemplary purpose. For reviews of propagation techniques using tissue culture, see Furukawa J., in "Schematic Diagramm: Textbook of Tissue Culture", Seibundo Shinkosha, 1985, Kako S., in "The Culture of Organs and Tissues of Horticulture Plants"0 Seibundo Shinkosha etc.

PROBLEMS TO BE SOLVED BY THE INVENTION

As described above, a large scale production of plants by tissue culture techniques has been developed for various kinds of plants. However, such techniques have several disadvantages such as insufficient rooting and low percentage in propagation by cutting, necessity of manual labor for cutting and rooting in adventifious shoot method, low conversion rate from somatic embryos to plantlets even if somatic embryos can be formed, and the like, and therefore such methods are still unsatisfactory for commercial application. The object of the present invention is to provide a technique which enables to produce young plants simply, reproducibly and efficiently without limitation by the species of the plants.

DISCLOSURE OF THE INVENTION

As a result of research and investigation about a large scale propagation of plants, namely about a portion of plants to be used for culture, medium compositions, culturing procedure, etc., the inventors have found that a cell mass capable of differenciating into a plant can be obtained by culturing a root in a liquid medium.

Namely, the present process for producing a plantlet comprises culturing a root as an explant in a liquid medium containing at least inorganic salts, a carbon source, and an auxin to induce the formation of a cell mass, then optionally culturing said cell mass in a similar liquid medium for further propagation, and thereafter culturing the resultant cell mass in a redifferentiation medium containing at least inorganic salts and a carbon source to produce a plantlet.

The invention will be described hereinbelow in detail.

PLANT OF THE MATTER

Any plant having roots may be employed in the present invention, including but not limited to dicotyledons and monocotyledons.

CELL MASS

The term "cell mass" used in the present invention refers to an independent unit having epidermis layer and obtained by culturing a root as an explant in a liquid medium, and not to a callus which is an aggregate of dedifferentiated cells. The shape of the cell mass includes a sphere, an ellipsoid, an indefined shape such as a fused shape of a sphere and an ellipsoid, and the like. Furthermore, the cell mass of some plant species may be morphologically identified as a spherical embryo, and becomes somatic embryo as culturing proceeds.

INDUCTION AND PROPAGATION OF CELL MASS, AND REGENERATION TO A PLANTLET

One of the preferred embodiments is described hereinafter, though culturing may be effected in any of suitable methods.

(a) Preparation of a Root

A root is used as a source of an explant for inducing the formation of a cell mass. Said root may be of any type including but not limited to a root of germinated seed, a tuber, a bulb, an adventitious root derived from a tissue of a leaf or a stem. The root may also be obtained by propagating a sterilized root. The explant from these origins is sterilized before use if necessary, by conventional methods such as treatment with ethanol, aqueous sodium hypochlorite solution, and the like.

(b) Induction of a Cell Mass

A liquid medium used for the induction of a cell mass from the root contains inorganic salts, a carbon source and an auxin as essential components, and additionally contains vitamins, amino acids and the like, if necessary. Concrete examples of the liquid medium are those prepared by adding an auxin to a basal medium conventionally used for plant tissue culture, for example Murashige & Skoog medium (MS medium), Linsmaier & Skoog medium (LS medium), Gamborg B-5 medium, etc. The composition of these known mediums are described, for example, by Harada H. and Komamine A., in "Tissue Culture of Plant Cells" pp390–391, Rikogakusha, 1984. The basal medium may be selected depending on the type of the plant to be used. For example, BDS medium (Dunstan, D. I. and Short, K. C., Physiologia Plantatum 41: 70–72, 1977) prepared by modifying B-5 medium may preferably be used for the plants belonging to the genus Allium.

As examples of the carbon source, sucrose, glucose, etc. may be mentioned, with preferred concentration of 5–100g/1. As examples of auxins, 2,4-D, naphthaleneacetic acid(NAA), indoleacetic acid(IAA), indolebutyric acid(IBA), and the like may be used alone or in combinations thereof. The concentration of the auxin may range from 0.0–50 mg/l 0.1–20 mg/l being preferred.

The pH of the medium is preferably adjusted to 5.0–6.5.

In addition, 5–150 g/l of a sugar alcohol such as mannitol and sorbitol may also be added to the above mentioned medium as an osmotic pressure regulator to achieve further improved results.

Cell mass may be obtained by culturing an explant of a root at about 15–35° C. after setting it in a liquid medium prepared as above. Though the induction of the formation of a cell mass may be carried out by static culture, it can more advantageously be effected by stirring the culture by force, for example, by shaking culture or rotation culture at 60–160rpm, or aeration culture, or aeration culture with stirring.

(c) Propagation of a Cell Mass

The cell mass as obtained in the step (b) may directly be used to produce a plantlet according to the step (e) described below. Alternatively, it may further be propagated in the step (c), as follows.

The cell mass obtained in the step (b) may be propagated by culturing it in a medium containing at least inorganic salts, a carbon source and an auxin, and optionally containing vitamins, amino acids, and the like. Specifically, said medium may be prepared by adding 5–100 g/l of sucrose as a carbon source, and 0.0–70 mg/l of an auxin, preferably 2,4-D or NAA, to the above described basal medium. Cytokinins such as benzyladenine(BA), kinetin(KN), Zeatin may also be added to the above medium to a concentration of 0.0–10 mg/l for better redifferentiation rate to a plantlet in subsequent step (e).

The redifferentiation rate may further be improved by the addition of 5–150 g/l of a sugar alcohol such as mannitol or sorbitol as an osmotic pressure regulating agent.

Preferably, culturing is conducted under forcible agitation such as in shaking culture or rotation culture.

(d) Post Culturing of the Cell Mass

From the cell mass as obtained in the step (b) or (c), a plantlet can be produced by the step (e) below. A post-culturing in this step may lead to an increased regeneration rate in the step (e).

Culturing of the cell mass as obtained in the step (b) or (c) in a liquid or on a solid medium prepared by adding inorganic salts, a carbon source and the like to the basal medium leads to the formation of a cell mass capable of regenerating more readily, or to the formation of a mature somatic embryo. A liquid or solid medium prepared by adding inorganic salts, a carbon source such as sucrose to a concentration of 0–80 g/l to a basal medium such as 1/10 X to 1 X MS medium may preferably be used. Agar, gellan gum, carrageenan, agarose, and the like may be used as a support for the solid medium in a conventional concentration, for example, 2–10 g/l for gellan gum.

Preferably, 5–50 g/l of a sugar alcohol such as mannitol or sorbitol is also added as an osmotic pressure regulating agent. (e) Regeneration of a Plantlet A plantlet may be obtained from the cell mass prepared in the step (b), (c) or (d), or from the somatic embryo derived therefrom, by culturing in a redifferentiation medium as described below.

The redifferentiation medium contains inorganic salts and a carbon source as essential ingredients and optionally contains vitamins, amino acids, etc. For example, a plantlet may be obtained by culturing the cell mass in a basal medium such as MS medium supplemented with 5–100 g/l of sucrose or glucose as a carbon source. An improved results may be obtained by adding 5–150 g/l of sugar alcohol such as mannitol, sorbitol, etc., 0.001–5 mg/l of a plant hormone such as IBA, NAA, KN and/or BA, or 0.5–10 mg/l of $GA_3$.

From the plantlets thus obtained, plants capable of growing vividly can be produced by acclimatizing them in a greenhouse maintained at a relative humidity of about 75–95%.

It is generally known that there are two types of calli originated from plant tissue, namely embryogenic callus capable of regenerating a plant and non-embryogenic callus incapable of growing into a plant. According to the present invention, plants can be obtained by culturing a root as an explant in a liquid medium containing at least inorganic salts, a carbon source and an auxin to induce the formation of a cell mass different from a callus, followed by further culturing of said cell mass to give a plant.

The following effects can be attained by the present invention.

Plantlets can be obtained simply, reproducibly and efficiently regardless of the plant species, according to the present invention.

EXAMPLE

The present invention is illustrated, but in no way limited, by the following Examples. It is intended that possible improvement and modification conceivable by those skilled in the art from the description of this application should be included in the present invention.

Example 1: Asparagus

About 50 mm of an apical portion was cut from young stem of *Asparagus officinalis* L. The surface of the section was sterilized with 70% ethanol and aqueous sodium hypochlorite solution (0.5 % effective concentration), and growing points were excised from the terminal bud and the lateral bud. A few rootlets grown aseptically therefrom to a length of 10–50 mm on MS medium (pH 5.8) containing 8 g/l of agar, 0.5 mg/l of kinetin and 0.2 mg/l of IBA were cut from the root collar, and set on 100 ml of MS liquid medium (pH 5.8) containing 2 mg/l of 2,4-D, 40 g/l of sucrose, and desirably 10 mM proline, 100 mg/l of casein hydrolysate and 30 g/l mannitol, in 500 ml conical flask, and cultured with shaking or rotation at 100 rpm with an illumination of about 3000 lux for 12 hours a day. Cell masses were formed 12 months later, and subcultured in the same medium as mentioned above for propagation.

The resultant cell masses were further subcultured in MS liquid medium containing 0.5–1 mg/l of 2,4-D and 30 g/l of sucrose for propagation. Additional incorporation of 30 g/l of sorbitol and/or 0.2 mg/l of kinetin to the medium results in increased propagation and redifferentiation into plantlets.

The propagated cell masses were placed on MS medium (pH 5.8) containing 30 g/l of sucrose and 4 g/l of gellan gum. After about 2 weeks, normal plantlets grew and showed vivid growth.

Comparison Example 1: Asparagus

The procedure of Example 1 was followed except that a solid medium containing 8 g/l of agar was used as an induction medium. Cell mass could scarcely be obtained.

Example 2: Parsley

The surface of a seed of *Petroselinum crispum* Nym. cultivar Paramount, was sterilized with 70% ethanol and aqueous sodium hypochlorite solution (0.5% effective concentration), and sown on MS medium (pH 5.8) containing 8 g/l of agar. The rootlets of the germinated seed were cut from the root collar, set in 70 ml of MS liquid medium (pH 5.8) containing 5 mg/l of 2,4-D and 30 g/l of sucrose in 300 ml conical flask, and cultured with shaking at 90 rpm with an illumination of about 3000 lux for 12 hours a day.

About 1 month later, cell masses produced were transferred onto MS medium (pH 5.8) containing 30 g/l of sucrose and 8 g/l of agar. Normal plantlets were obtained via somatic embryo of torpedo shape.

Example 3: Garlic

The surface of a seed bulb of Allium sativum L., cultivar White 6 Cloves, was sterilized with 70% ethanol and aqueous sodium hypochlorite solution (0.5% effective concentration). The growing points were excised 0.2 mm in length, set on BDS agar medium (pH 5.8) containing 0.01 mg/l of NAA, 0.01 mg/l of BA and 30 g/l of sucrose. About 3 months later, a few rootlets of 30–50 mm in length grown from the regenerated plant were cut from the root collar, and set in 70 ml of BDS liquid medium (pH 5.8) containing 2 mg/l of 2,4-D and 30 g/l of sucrose, in 300-ml conical flask, and cultured with shaking at 120 rpm with an illumination of about 3000 lux for 12 hours a day.

About 1 month later, the resultant cell masses were subcultured in the fresh medium as mentioned above and allowed to propagate. The resultant cell masses were further subcultured in BDS medium (pH 5.8) containing 20 g/l of sucrose, 0.1 mg/l of kinetin and 50 g/l of mannitol, post-cultured for about 1 week, and set on BDS solid medium (DH 5.8) containing 20 g/l of sucrose. About 2 weeks later, plantlets were found to appear and showed vivid growth.

The above described post-culturing is not essential step. A plantlet could also be obtained by culturing the cell mass on BDS solid medium (pH 5.8) containing 0.5 mg/l of NAA, 2 mg/l of kinetin and 30 g/l of sucrose.

Comparison Example 2: Garlic

The procedure of Example 3 was followed except that a solid medium containing 8 g/l of agar was used as an induction medium. Cell mass could scarcely be obtained.

Example 4: Lily

The rootlets of 15–30 mm in length generated from a bulb of *Lilium longiflorum* Thunb., cultivar Chotaro, maintained on MS medium (pH 5.8) containing 30 g/l of sucrose and 8 g/l of agar were cultured with shaking in 100 ml of MS liquid medium (pH 5.8) containing 0.1 mg/l of NAA, 100 mg/l of casein hydrolysate, 30 g/l of mannitol and 10 g/l of sucrose, in 500 ml conical flask.

About 2 months later, resultant cell masses were set on MS medium (pH 5.8) containing 30 g/l of sucrose and 8 g/l of agar. Plantlets were obtained about 2 months later.

Example 5: Onion

A seed of *Allium cepa* L. was sterilized with 70% ethanol and aqueous sodium hypochlorite solution (0.5% effective concentration), and sown on MS medium (pH 5.8) containing 8 g/l of agar and 30 g/l of sucrose. The roots of 30–50 mm in length including a growing point were cut from the germinated seed, and set in MS liquid medium (pH 5.8) containing 10 g/l of sucrose, 30 g/l of mannitol, 2 mg/l of 2,4-D, 100 mg/l of casein hydrolysate and 12 mM proline. The density of setting was 3 rootlets per 100 ml of the medium described above, in 500 ml conical flask. After culturing with shaking at 80 rpm for about 2 months, cell masses of various shapes including a sphere and a heart shapes, etc. were formed. 0.5 g each of the cell masses was then subcultured in a fresh medium of the same composition every 4 weeks.

The cell masses obtained as above were transferred to MS liquid medium (pH 5.8) containing 10 g/l of sucrose, 80 g/l of mannitol, 1 mg/l of 2,4-D, 100 mg/l of casein hydrolysate and 12 mM proline, and cultured for 4 weeks followed by setting on MS medium (pH 5.8) containing 50 g/l of sucrose and 8 g/l of agar. After about 2 weeks, a number of plantlets were regenerated from these cell masses. Though these plantlets grew normally without any further procedure, they grew more vividly after transplantation onto MS medium (pH 5.8) containing 30 g/l of sucrose and 8g/l of agar.

Example 6:

A seed of Japanese leek (*Allium fistulosum* L.) was sterilized with 70% ethanol and aqueous sodium hypochlorite solution (0.5% effective concentration), and sown on MS medium (pH 5.8) containing 8 g/l of agar and 30 g/l of sucrose. The roots of 20–40 mm in length including a growing point were cut from the germinated seed, and set in MS liquid medium (pH 5.8) containing 10 g/l of sucrose, 30 g/l of mannitol, 0.5 mg/l of 2,4-D, 100 mg/l of casein hydrolysate and 12 mM proline. The density of setting was 3–5 rootlets per 100 ml medium, in 500 ml conical flask. After culturing at 20° C. in the dark with shaking at 80 rpm for about 2 months, cell masses of various shapes including a sphere, etc., were obtained. The resultant cell masses were then subcultured every 4 weeks in the above medium containing 2 mg/l of benzyladenine for propagation.

The cell masses obtained as above were set on MS medium (pH 5.8) containing 2 g/l of Gelrite$^R$, 10 g/l of sucrose, 30 g/l of mannitol and 100 mg/l of casein hydrolysate. About 3–4 weeks later, plantlets were obtained.

What is claimed is:

1. A process for producing a plantlet which comprises culturing a root as an explant in a liquid induction medium comprising inorganic salts, a carbon source and an auxin, wherein the concentration of said auxin is in a range from 0.1 to 5 mg./liter, to induce the formation of a cell mass, and culturing the resultant cell mass in a redifferentiation medium, comprising inorganic salts and a carbon source, to produce a plantlet.

2. A process for producing a plantlet which comprises culturing a root as an explant in a liquid induction medium comprising inorganic salts, a carbon source and an auxin, wherein the concentration of said auxin is in a range from 0.1 to 5 mg./liter, to induce the formation of a cell mass, then further culturing said cell mass in a liquid propagation medium comprising inorganic salts and a carbon source for further propagation, and subsequently culturing the resultant cell mass in a redifferentiation medium comprising inorganic salts and a carbon source, to produce a plantlet.

3. The process of claim 1 or 2, wherein said root is derived from a plant belonging to the family Liliaceae or the family Umbelliferae.

4. The process of claim 1 or 2 further comprising agitating the medium.

5. The process of claim 4 wherein said agitating is performed by stirring.

6. The process of claim 4 wherein said agitating is performed by rotation.

7. The process of claim 4 wherein said agitating is performed by shaking.

* * * * *